US00PP37385P2

(12) United States Plant Patent
Smith

(10) Patent No.: US PP37,385 P2
(45) Date of Patent: Apr. 28, 2026

(54) ***PAEONIA* PLANT NAMED 'Smithopus12'**

(50) Latin Name: ***Paeonia* hybrid**
Varietal Denomination: Smithopus12

(71) Applicant: Donald R. Smith, Fairfield, CT (US)

(72) Inventor: Donald R. Smith, Fairfield, CT (US)

( * ) Notice: Subject to any disclaimer, the term of this patent is extended or adjusted under 35 U.S.C. 154(b) by 0 days.

(21) Appl. No.: 19/264,111

(22) Filed: Jul. 9, 2025

(51) Int. Cl.
*A01H 6/00* (2018.01)
*A01H 5/02* (2018.01)

(52) U.S. Cl.
USPC ..... Plt./316

(58) Field of Classification Search
USPC ..... Plt./316
CPC ..... A01H 6/00; A01H 5/02
See application file for complete search history.

*Primary Examiner* — Keith O. Robinson

(57) ABSTRACT

A new and distinct cultivar of intersectional hybrid (Itoh) *Paeonia* plant named 'Smithopus12' is disclosed, characterized by large light yellowish pink colored flowers with bright pink streaks of single or semi-double form carried on strong stems, which present the flowers above and beyond the foliage. Plants have, dissected foliage, which lasts through the fall and is also disease resistant. Plants have a symmetrical, compact plant habit/shape which is excellent in the landscape. The new variety is an intersectional hybrid (Itoh) *Paeonia* normally produced as an outdoor ornamental garden plant.

2 Drawing Sheets

Figure 1:
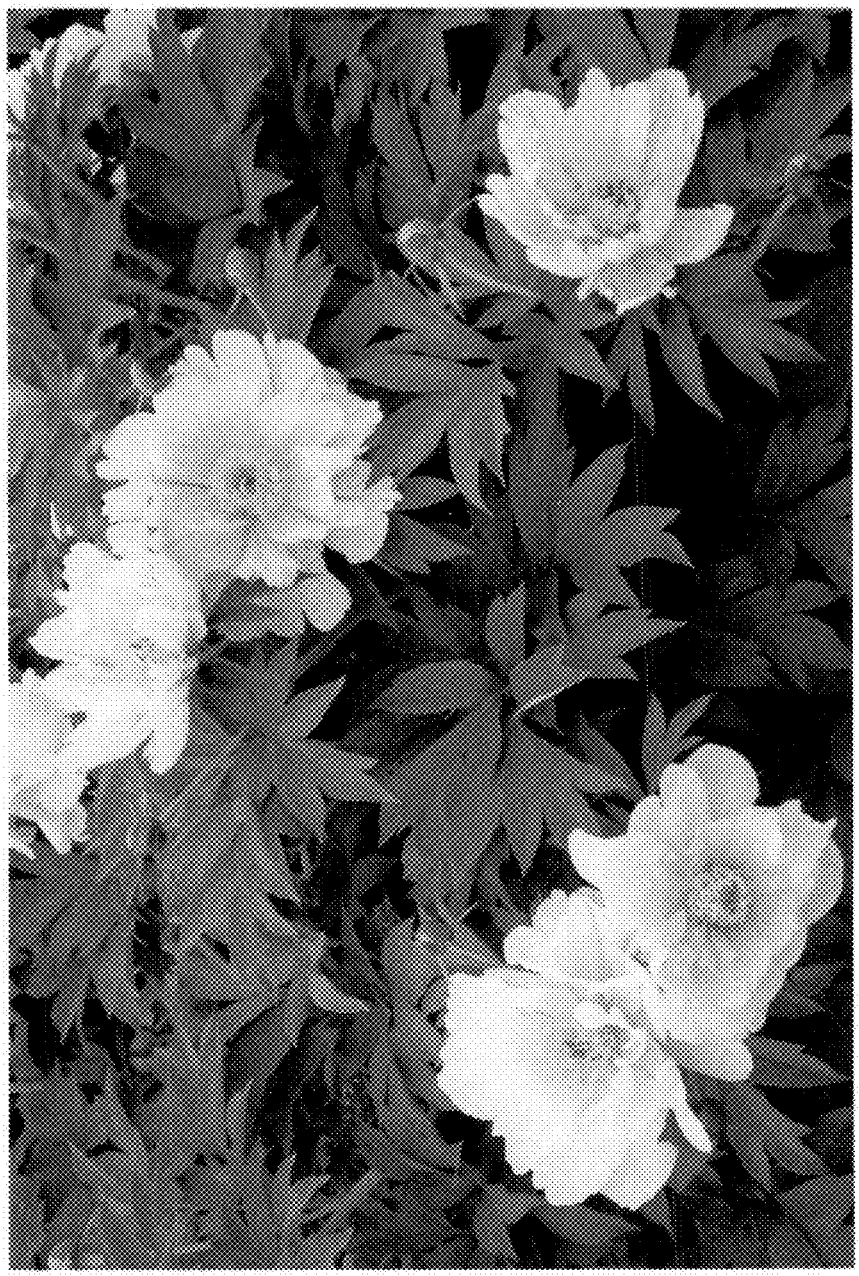

Latin name of the genus and species: *Paeonia* hybrid.
Variety denomination: 'Smithopus12'.

BACKGROUND OF THE INVENTION

The new cultivar is a product of a planned breeding program conducted by the inventor to produce new *Paeonia* hybrid cultivars with strong stems, large panicles, compact habits, and attractive flower aging. The crossing resulting in the new cultivar was made in summer of 2011 in a backyard in Windham, NH.

The seed parent is the cultivar *Paeonia* 'Martha W', unpatented. The pollen parent is the cultivar *Paeonia* 'Golden Experience', an unpatented tree peony hybrid. The new cultivar was found and selected by the inventor in 2017 in the same backyard in Windham, NH. Asexual reproduction of the new cultivar 'Smithopus12' was first performed at a research laboratory during 2018 in the Netherlands by tissue culture. Through subsequent confidential propagation, multiple additional generations have been reproduced, having shown that the unique features of this cultivar are stable and reproduced true to type.

SUMMARY OF THE INVENTION

The cultivar 'Smithopus12' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Smithopus12'. These characteristics in combination distinguish 'Smithopus12' as a new and distinct *Paeonia* cultivar:

1. New cultivar is an intersectional hybrid (Itoh) peony from a cross of an herbaceous peony (lactiflora) with a hybrid tree peony.

2. It is a sterile first-generation hybrid with triploid (3n) ploidy level.
3. New cultivar has large light yellowish pink colored flowers with bright pink streaks of semi-double to single form carried on strong stems, which present the flowers above and beyond the foliage.
4. New cultivar has very attractive, dissected foliage, which lasts through the fall and is also highly disease resistant.
5. New cultivar has a symmetrical, compact plant habit/shape and makes an ideal landscape plant.

PARENT COMPARISONS

Plants of 'Smithopus12' are similar to plants of the seed parent in most horticultural characteristics, however, plants of 'Smithopus12' differ in the following:

1. Seed parent has fully herbaceous stems and growth habit, whereas the new cultivar has stronger semi-woody to woody stems and many above-ground buds, yet grows primarily as an herbaceous plant.
2. Seed parent has pink flowers of single form with 11-13 petals, whereas the new cultivar has semi-double to single flowers colored light yellowish pink with bright pink streaks with about 12 to 20 petals.
3. Seed parent blooms 1-2 weeks later than the new cultivar.
4. Seed parent has many lateral flowers per stem, whereas the new cultivar has only 1 or 2.
5. Seed parent is highly fertile both ways, whereas the new cultivar is a sterile triploid.

Plants of 'Smithopus12' are similar to plants of the pollen parent in most horticultural characteristics, however, plants of 'Smithopus12' differ in the following:

1. The new variety has light yellowish pink colored flowers whereas 'Golden Experience' has bright yellow flowers.

2. The pollen parent has flowers with a single row of petals, whereas the new variety has two rows or more.
3. Pollen parent is a woody tree peony hybrid that has winter hardy, woody stems, whereas the new variety has semi-woody stems and are much less winter hardy.
4. Pollen parent has more upright, shrub-like plant and growth habit, whereas the new variety has mostly herbaceous habit.
5. Pollen parent blooms 1-2 weeks before the new variety.

COMMERCIAL COMPARISON

Plants of 'Smithopus12' can be compared to plants of the commercial cultivar *Paeonia* intersectional hybrid 'Magical Mystery Tour', unpatented. Plants of 'Smithopus12' are similar to plants of 'Magical Mystery Tour' in most horticultural characteristics, however, plants of 'Smithopus12' differ in the following:

1. 'Magical Mystery Tour' has coral to creamy pink flower; the new cultivar has light yellowish pink colored flowers with bright pink streaks.
2. The new cultivar is more floriferous than 'Magical Mystery Tour', as a result of having more flowers from lateral stems.
3. The new cultivar has flowers that are more double than 'Magical Mystery Tour'.

Plants of 'Smithopus12' can be compared to plants of the commercial cultivar *Paeonia* intersectional hybrid 'Singing in the Rain II', U.S. Plant Pat. No. 19,374. Plants of 'Smithopus12' are similar to plants of 'Singing in the Rain II' in most horticultural characteristics, however, plants of 'Smithopus12' differ in the following:

1. 'Singing in the Rain II' has cream/yellow to light orange petals; petals of the new cultivar are light yellowish pink colored flowers with bright pink streaks.
2. 'Singing in the Rain II' has smaller flowers than the new cultivar.
3. 'Singing in the Rain II' has more flowers per stem than the new cultivar.

BRIEF DESCRIPTION OF THE PHOTOGRAPHS

The accompanying photograph in FIG. 1 illustrates in full color a typical plant of 'Smithopus12' grown in a field in Fairfield, CT. This plant is approximately 3 years old.

Figure 2:
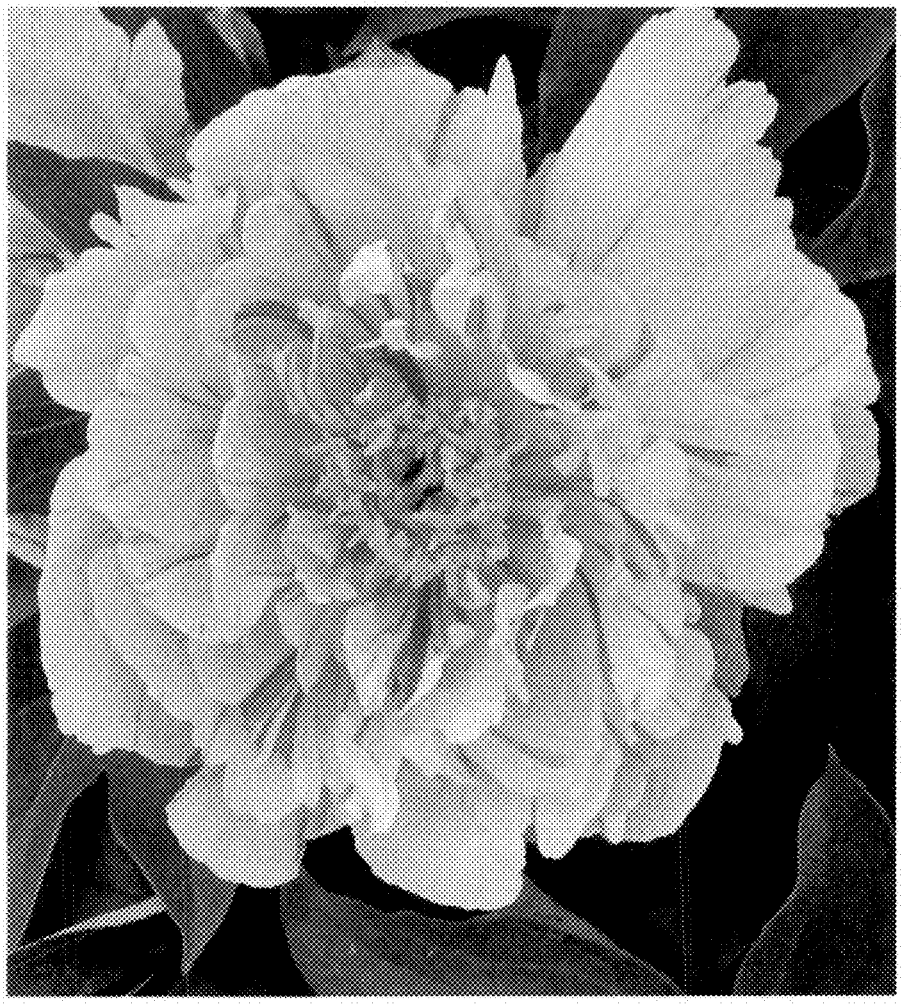

FIG. 2 illustrates in full color a close-up of a mature flower of 'Smithopus12'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Smithopus12' plants grown outdoors in Camarillo, CA. The plants were 2 to 3 years old from large tubers, grown in 5-gallon pots. Temperatures ranged from 5° C. to 10° C. at night to 12° C. to 30° C. during the day. No artificial light, photoperiodic treatments were given to the plants. Measurements and numerical values represent averages of typical plant types.

Botanical classification: *Paeonia* hybrid 'Smithopus12'.

PROPAGATION

Typically by shoot tissue culture.

Root description: Freely branching storage root with numerous feeder roots. Roots various shades of tan and brown, not accurately measured with a color chart.

Tubers: Elongated, typically 4 to 10 cm long and 2 to 4 cm in diameter. Colored near Greyed-Orange 166C.

PLANT

Growth habit: Vigorous perennial herbaceous shrub. Semi-upright growth habit.

Height: Approximately 65 cm at opening of first flower.

Plant spread: Approximately 105 cm.

Stems:

*Length*.—Approximately 65 to 70 cm.

*Diameter*.—Average range 6 to 7 mm.

*Strength*.—Strong.

*Internode length*.—6 to 13 cm, variable, but longer near top of stem.

*Color*.—Near RHS Green 138D.

*Texture*.—Glabrous.

Age of plant described: Approximately 2 to 3 years.

FOLIAGE

Leaf: Alternate, pinnate compound, with an overall circular to ovate shape, which is slightly wider than long. Average fully expanded leaf 25 cm long and 30 cm wide, excluding the petiole. Horizontal to semi-erect attitude.

Primary leaflets:

*Shape*.—Obovate.

*Quantity and arrangement*.—3 primary leaflets further divided into 3 to 5 deeply divided secondary leaflets. All leaflets sessile.

*Length*.—Average range 15 to 17 cm.

*Width*.—Average range 18 to 20 cm.

Individual primary leaflet blades:

*Shape of blade*.—Broad ovate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very slightly reflexed downward.

Individual secondary leaflet blades:

*Shape of blade*.—Oblanceolate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very minutely reflexed downward.

*Color*.—Emerging. Upper side: Near RHS Green 138B. Under side: Near RHS Green 138C. Young. Upper side: Near RHS Green 137D. Under side:

Near RHS Green 138A. Mature. Upper side: Near RHS Green 137A. Under side: Near RHS Green 138D.

*Venation*.—Type: Pinnate. Venation color upper side: Near RHS Yellow-Green 149C. Venation color under side: Near RHS Green 149C.

*Petiole*.—Length: Average 10-12 cm. Diameter: 5 mm. Color: Near RHS Yellow-Green 146D. Texture: Glabrous.

FLOWER

Natural flowering season: Flowering begins mid to late May in Southwestern Connecticut. Flowering extends over a period of approximately 3 weeks.

Inflorescence type and habit: Double form with conspicuous stamens. 3 to 4 loose whorls. Shape regularly round. Erect flower attitude.

Flower longevity on plant: Approximately 8 to 12 days on the plant. Varies considerably with environmental conditions.

Quantity of flowers: 4 to 5 per stem. 5 to 7 flowering stems per plant.

Flower size:

*Diameter*.—Approximately 12.5-15 cm.

*Depth*.—Approximately 6 cm. (Flower height).

Peduncle:

*Length*.—Approximately 6-10 cm.

*Diameter*.—Approximately 5 mm.

*Color*.—Near RHS Yellow-Green 144C.

*Strength*.—Strong.

*Texture*.—Glabrous.

Petals:

*Petal arrangement*.—2 to 3 loose whorls of about 12 to 20 petals.

*Size*.—Length: Average 6.5 cm. Width: Average 5 cm.

*Shape*.—Obovate.

*Margin*.—Entire.

*Apex*.—Emarginate.

*Base*.—Broad attenuate.

*Texture*.—Smooth, glabrous all surfaces.

*Aspect*.—Moderately reflexed downward.

*Petal blotch*.—Not present.

Color:

*Petals*.—When opening: Opening: Upper surface: Near RHS Yellow-Orange 20D. Streaks Red 53C. Lower surface: Near RHS Yellow-Orange 18D. Streaks Red 53D. Fully opened: Upper surface: Near RHS Yellow 2D Streaks Red 53D. Lower surface: Near RHS Yellow 4D. Streaks Red 54A.

Petaloids: Not present.

Bud:

*Shape*.—Oblate.

*Length*.—Approximately 2.3 cm.

*Diameter*.—Approximately 1.9 cm.

*Color*.—Near RHS Yellow-Green 139C flushed Red-Purple 61A-B.

Sepals:

*Quantity*.—Usually 3.

*Length*.—Variable, each different, (20-35 cm).

*Width*.—Variable, each different, (30-35 cm).

*Shape*.—Deltate.

*Aspect*.—Flat.

*Attitude*.—Horizontal.

*Apex*.—Acute.

*Base*.—Truncate.

*Margin*.—Entire.

*Color*.—Interior Surface: RHS Green 138B. Exterior Surface: RHS Green 139C.

*Texture*.—Glabrous.

Fragrance: Light, pleasant, lemon-like.

REPRODUCTIVE ORGANS

Androecium:

Stamens:

*Quantity*.—100 to 120.

*Length*.—28 to 30 mm.

*Color*.—Yellow 13B.

Anthers:

*Shape*.—Linear or curled.

*Length*.—2.5 mm.

*Color*.—Yellow 13B.

Gynoecium:

Pistil:

*Type*.—Compound. Carpel and stigma only (no style).

*Number*.—3-5, average of 4, (for terminal flowers=3-4, for axillary flowers=4-5).

*Carpel length*.—1.8 cm.

*Carpel width*.—0.8 cm.

*Carpel pubescence*.—Medium.

*Openness of disc*.—Partly open.

*Disc color*.—Green 143D.

*Stigma*.—Size: 3 mm high and 4 mm wide. Shape: Irregular cuneate with an undulated tip. Color: Near RHS Red-Purple 63A.

*Ovary color*.—Near RHS Green 146A.

OTHER CHARACTERISTICS

Disease and pest resistance: Observed resistance to foliar diseases of *Paeonia*. Typical foliar diseases of *Paeonia* include *Botrytis paeoniae, Graphiopsis chlorocephala* and *Phytophthora*. sp. No additional resistance nor susceptibility to the normal diseases and pests of *Paeonia* have been observed.

Temperature tolerance: Typically USDA Zones 3 to 9.

Fruit/seed production: Not observed.

What is claimed is:

1. A new and distinct cultivar of *Paeonia* plant named 'Smithopus12' as herein illustrated and described.

* * * * *